US00PP25450P2

(12) United States Plant Patent
Hartman

(10) Patent No.: US PP25,450 P2
(45) Date of Patent: Apr. 14, 2015

(54) ***CALADIUM* PLANT NAMED 'LEMON BLUSH'**

(50) Latin Name: *Caladium×hortulanum*
Varietal Denomination: Lemon Blush

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 115 days.

(21) Appl. No.: 13/986,543

(22) Filed: May 14, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Annette Para
(74) *Attorney, Agent, or Firm* — C. A. Whealy

(57) ABSTRACT

A new and distinct cultivar of *Caladium* plant named 'Lemon Blush', characterized by its intermediate to tall, upright and uniformly mounding plant habit; vigorous growth habit and rapid growth rate; fancy-type leaves that are chartreuse to lime green in color with rose red-colored centers; with development, rose red-colored areas can cover the entire leaf surface; and good landscape performance.

4 Drawing Sheets

Botanical designation: *Caladium×hortulanum.*
Cultivar denomination: 'LEMON BLUSH'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Lemon Blush'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2008 in Avon Park, Fla. of *Caladium×hortulanum* 'Miss Muffet', not patented, as the female, or seed, parent with *Caladium×hortulanum* 'Florida Red Ruffles', disclosed in U.S. Plant Pat. No. 13,136, the male, or pollen, parent. The new *Caladium* plant was discovered and selected by the Inventor as a single plant within the progeny of the stated cross-pollination in a controlled outdoor nursery environment in Zolfo Springs, Fla. in September, 2009.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April 15, 2010 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Lemon Blush'. These characteristics in combination distinguish 'Lemon Blush' as a new and distinct *Caladium* plant:

1. Intermediate to tall, upright and uniformly mounding plant habit.
2. Vigorous growth habit and rapid growth rate.
3. Fancy-type leaves that are chartreuse to lime green in color with rose red-colored centers; with development, rose red-colored areas can cover the entire leaf surface.
4. Good landscape performance.

Plants of the new *Caladium* differ primarily from plants of the female parent, 'Miss Muffet', in leaf color as plants of 'Miss Muffet' have pale green-colored leaves with pink and dark red-colored spots. In addition, plants of the new *Caladium* are taller than plants of 'Miss Muffet'.

Plants of the new *Caladium* differ primarily from plants of the male parent, 'Florida Red Ruffles', in leaf shape and color as plants of 'Florida Red Ruffles' have lance-type leaves that are dark red in color with dark green-colored margins. In addition, plants of the new *Caladium* are larger and grow faster than plants of 'Florida Red Ruffles'.

Plants of the new *Caladium* can be compared to plants of *Caladium×hortulanum* 'Raspberry Moon', disclosed in U.S. Plant Pat. No. 20,069. In side-by-side comparisons, plants of the new *Caladium* differed primarily from plants of 'Raspberry Moon' in the following characteristics:

1. Plants of the new *Caladium* were slightly shorter than plants of 'Raspberry Moon'.
2. Plants of the new *Caladium* and 'Raspberry Moon' differed in leaf color as leaves of plants of 'Raspberry Moon' were lime green in color with random dark red purple and medium green-colored spots and blotches.

Plants of the new *Caladium* can be compared to plants of *Caladium×hortulanum* 'Scarlet Pimpernel', not patented. In side-by-side comparisons, plants of the new *Caladium* differed primarily from plants of 'Scarlet Pimpernel' in the following characteristics:

1. Plants of the new *Caladium* grew faster and produced finished plants about one week earlier than plants of 'Scarlet Pimpernel'.
2. Plants of the new *Caladium* had broader leaves than plants of 'Scarlet Pimpernel'.
3. Plants of the new *Caladium* and 'Scarlet Pimpernel' differed in leaf color as leaves of plants of 'Scarlet Pimpernel' were lime green in color with rose pink to purplish-colored centers and random occasional green-colored blotches.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Lemon Blush' in a 15-cm container and grown in a shadehouse.

The photograph at the top of the second sheet is a comparison view of typical plants of 'Lemon Blush' grown in 15-cm containers; the plant on the left has not had its tuber de-eyed and the plant on the right has had its tuber de-eyed prior to planting.

The photograph at the bottom of the second sheet is a close-up view of a typical inflorescence of 'Lemon Blush'.

The photograph at the top of the third sheet is a close-up view of typical plants of 'Lemon Blush' grown in an open field.

The photograph at the bottom of the third sheet is a close-up view of typical freshly-harvested tubers and roots of 'Lemon Blush'.

The photograph at the top of the fourth sheet is a comparison view of typical potted plants of 'Raspberry Moon' (left), 'Lemon Blush' (center) and 'Scarlet Pimpernel' (right).

The photograph at the bottom of the fourth sheet is a comparison view of typical potted plants of the female parent, 'Miss Muffet' (left), 'Lemon Blush' (center) and the male parent, 'Florida Red Ruffles' (right).

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds in an outdoor nursery in Crewsville, Fla. The plants were grown under cultural practices typical of commercial shadehouse and outdoor nursery production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were eight weeks old and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Lemon Blush'.

Parentage:

*Female, or seed, parent.*—*Caladium×hortulanum* 'Miss Muffet', not patented.

*Male, or pollen, parent.*—*Caladium×hortulanum* 'Florida Red Ruffles', disclosed in U.S. Plant Pat. No. 13,136.

Propagation:

*Type*.—By "chipping" the tubers.

*Time to initiate roots, summer*.—About seven to ten days at 32° C.

*Time to initiate roots, winter*.—About two to three weeks at 24° C.

*Tuber description* (*outdoor nursery-grown plants*).—Appearance: Multi-segmented and somewhat flattened; individual segments ovate to elliptic in shape. Height: About 2.4 cm. Diameter: About 2.7 cm to 3.1 cm. Segment height: About 1.4 cm. Segment diameter: About 1.2 cm. Texture: Thick, starchy; somewhat brittle. Color: Epidermis, freshly-harvested: Close to 199A and N199B. Epidermis, dried: Close to 200A to 200B. Cortical tissue: Close to 8C to 8D. Axillary buds: Close to 36B to 36C. Root description: Thick, fleshy contractile roots; color, close to 155C. Rooting habit: Few lateral branches; moderately dense.

Plant description:

*Plant type*.—Herbaceous perennial; suitable as a potted plant in containers 15-cm to 25-cm and suitable as a landscape plant in shaded areas.

*Plant and growth habit*.—Intermediate to tall, upright and uniformly mounding plant habit; vigorous and dense growth habit; rapid growth rate, potted plants in finished or saleable form in about six weeks after planting tubers; leaf petioles and leaves arise from one or more growing points on tubers; petioles mostly upright and arching outwardly with development.

*Plant height, from soil level to top of foliar plane, shadehouse-grown potted plants*.—About 34 cm to 41 cm.

*Plant height, from soil level to top of inflorescences, shadehouse-grown potted plants*.—About 42.5 cm.

*Plant diameter or spread, shadehouse-grown potted plants*.—About 40 cm to 54 cm.

*Number of clumps per plant, shadehouse-grown potted plants*.—About three to four from de-eyed tubers.

*Cataphylls, shadehouse-grown potted plants*.—Length: About 4.2 cm to 5.5 cm. Width: About 1.5 cm to 1.8 cm. Shape: Wedge-shaped. Apex: Obtuse. Base: Sheathing the stem. Color, outer surface: Close to N170D and 196C tinged with close to 182D; stippled, streaked and tessellated with close to N200A and tinged with close to 147A; with development, color becoming closer to 165D and 199A. Color, inner surface: Close to 155C; outer surface colors and patterns visible.

Foliage description:

*Arrangement and type*.—Alternate; simple; fancy-type.

*Length, shadehouse-grown potted plants*.—About 15 cm to 26 cm.

*Width, shadehouse-grown potted plants, flattened*.—About 16 cm to 20.5 cm.

*Shape*.—Broadly ovate.

*Apex*.—Cuspidate to obtuse.

*Base*.—Sagittate, peltate.

*Margin*.—Entire; mostly flat with some broad undulations.

*Texture, upper surface*.—Somewhat rugose, glabrous; leathery; dull sheen.

*Texture, lower surface*.—Smooth, glabrous; glaucous.

*Venation pattern*.—Pinnate.

*Color, shadehouse-grown potted plants*.—Developing leaves, upper surface: Background color: Central areas, close to 185B and 60A; marginal areas, close to 144D and 193A. Basal notch: Close to 187B. Midvein and primary venation: Close to 60A and 185A. Secondary venation: Close to 146A. Developing leaves, lower surface: Background color: Central areas, close to 184B; transitional areas, close to 193A and 158D; marginal areas, close to 191A to 191B; margins, close to 187B. Basal notch: Close to 187B. Midvein: Close to 184B and 181D. Primary venation: Close to 147C and 184B. Fully expanded leaves, upper surface: Background color: Central areas, close to 185A to 185B; transitional areas, close to 184B to 184C mottled with close to 145D; marginal areas, close to 145D and 193A; with development, virtually entire leaf surface becomes blotched, mottled and/or flushed with close to 185A to 185B, 184A to 184C and 183C; remaining green-colored areas, close to 147A and 146B to 146C. Basal notch: Close to 187C. Midvein and primary venation: Close to 60A and 185A. Secondary venation: Close to 146A. Fully expanded leaves, lower surface: Background color: Central areas, close to 184B; transitional areas, close to 193C and 157A; marginal areas, close to 193B and 145D; margins, close to 187B. Basal notch: Close to 187B. Midvein and primary venation: Close to 182C and 184B to 184C. Primary venation: Close to 147C and 184B.

*Petiole*.—Aspect: Initially upright and straight; with development, leaning outwardly and curving; flexible. Length, shadehouse-grown potted plants: About 23 cm to 32 cm. Diameter, distal, shadehouse-grown potted plants: About 4 mm to 6 mm. Diameter, proximal, shadehouse-grown potted plants: About 7.5 mm to 11 mm. Color, shadehouse-grown potted plants: Just below leaf and petiole junction, close to 182D streaked with close to 181C; proximally, close to N170D and 181C to 181D, stippled and streaked with close to 200A and tinged with close to 147A. Wing length, shadehouse-grown potted plants: About 5.5 cm to 6 cm. Wing diameter, shadehouse-grown potted plants: About 9 mm to 11 mm. Wing color, shadehouse-grown potted plants, outer surface: Close to N170D and 196C tinged with close to 182D, stippled and streaked with close to N200A and tinged with close to 147A. Wing color, shadehouse-grown potted plants, inner surface: Close to 196C to 196D; outer surface colors and patterns visible.

Inflorescence description: Inflorescences observed on eleven week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the lower one-third of the spadix; male flowers develop on the upper two-thirds of the spadix; sterile flowers develop at junction of female and male flower zones; near this junction, the spathe constricts and surrounds and encloses the female flowers; spathe open and cupped around male flowers.

*Fragrance*.—Night fragrant; sweet jasmine-like fragrance with camphor-like notes.

*Natural flowering season and flower longevity*.—Plants of the new *Caladium* typically flower during the spring or early summer in central Florida; flowers develop about eleven weeks after growth commences; inflorescences last about three days before fading; inflorescences persistent.

*Spathe*.—Length, overall: About 12.1 cm. Length, distal open portion: About 7.8 cm. Length, proximal closed portion: About 4.3 cm. Width, distal open portion: About 4 cm. Width, at constriction: About 1.6 cm. Width, proximal closed portion: About 3.2 cm. Shape: Ovate to elliptic. Apex: Acuminate. Base: Tapering to the peduncle. Margin: Entire. Texture, front and rear surfaces: Smooth, glabrous. Color, front surface: Distal open portion: Close to 155B; with development, color becoming closer to 200D. Proximal closed portion: Close to 148C and 147C; proximally tinged with close to 187A; color does not change with development. Color, rear surface: Distal open portion: Close to 155C. Proximal closed portion: Close to 147B variably streaked with close to 146B and 147D and variably tinged with close to 183D.

*Spadix*.—Length: About 8 cm. Length, male flower zone: About 5.8 cm. Length, sterile zone: About 1.3 cm. Length, female flower zone: About 2.2 cm. Diameter, male flower zone: About 1.3 cm. Diameter, sterile flower zone: About 8 mm. Diameter, female flower zone: About 1.2 cm. Shape: Columnar, spindle-shaped. Apex: Obtuse. Base: Obtuse. Aspect: Upright. Color, mature, male zone: Close to 159C to 159D. Color, mature, sterile zone: Close to 159C to 159D. Color, mature, female zone: Close to 19D with close to 162D. Male flowers: Quantity per spadix: About 188. Shape: Obovate. Height: About 3 mm. Diameter: About 3.5 mm. Pollen amount: Abundant. Pollen color: Close to 8D. Female flowers: Quantity per spadix: About 170. Shape: Obovate. Height: About 3 mm. Diameter: About 2 mm. Stigma color: Close to 19D. Ovary color: Close to 155C to 155D.

*Scape*.—Length: About 30.4 cm. Diameter: About 8 mm. Strength: Sturdy; flexible. Aspect: Mostly erect. Texture: Smooth, glabrous; glaucous. Color: Close to 147C and 195B sparsely stippled and streaked with close to 200A; distally, close to 147C faintly tinged with close to 148B.

*Seeds and fruits*.—Seed and fruit development have not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Lemon Blush' as illustrated and described.

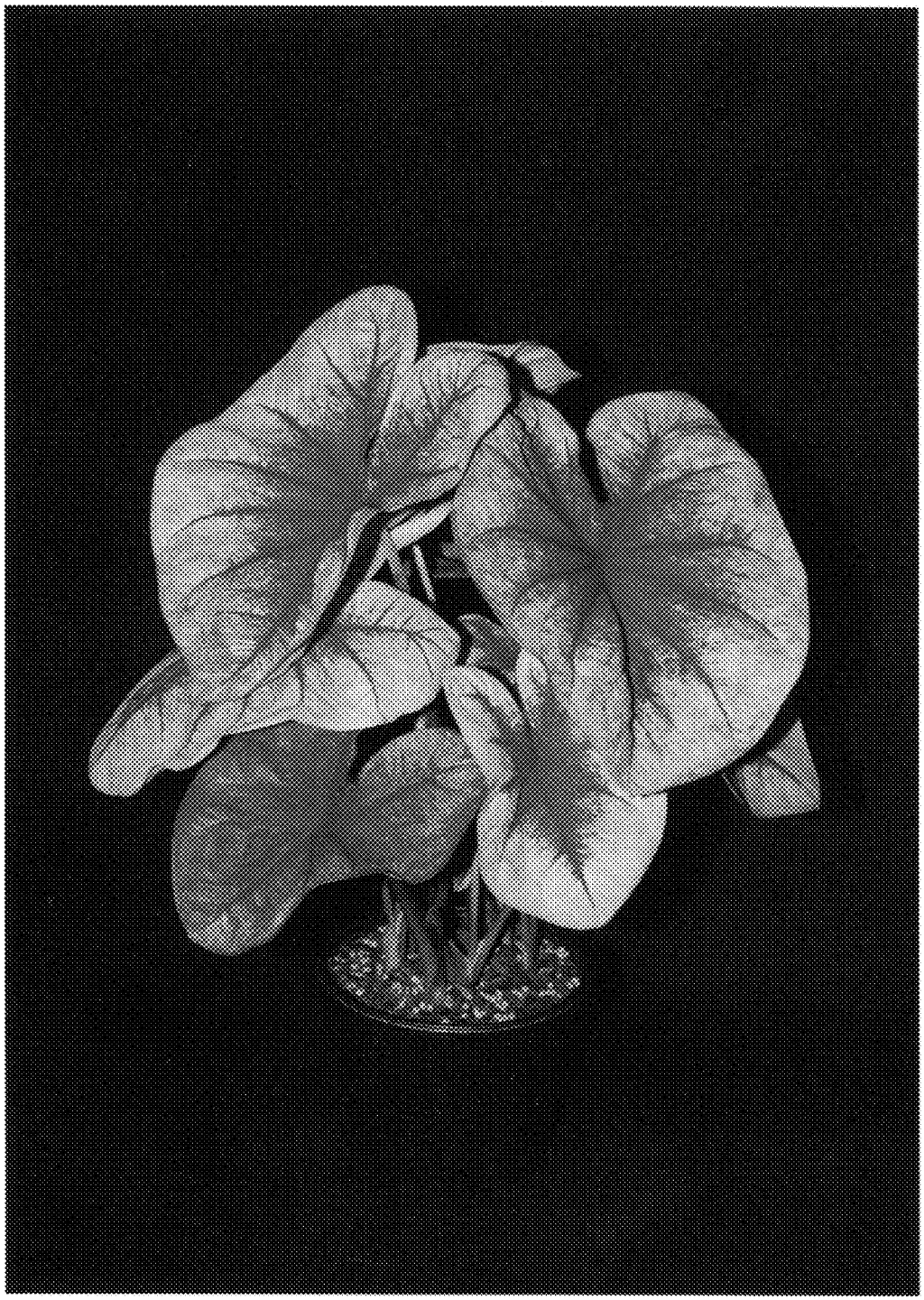

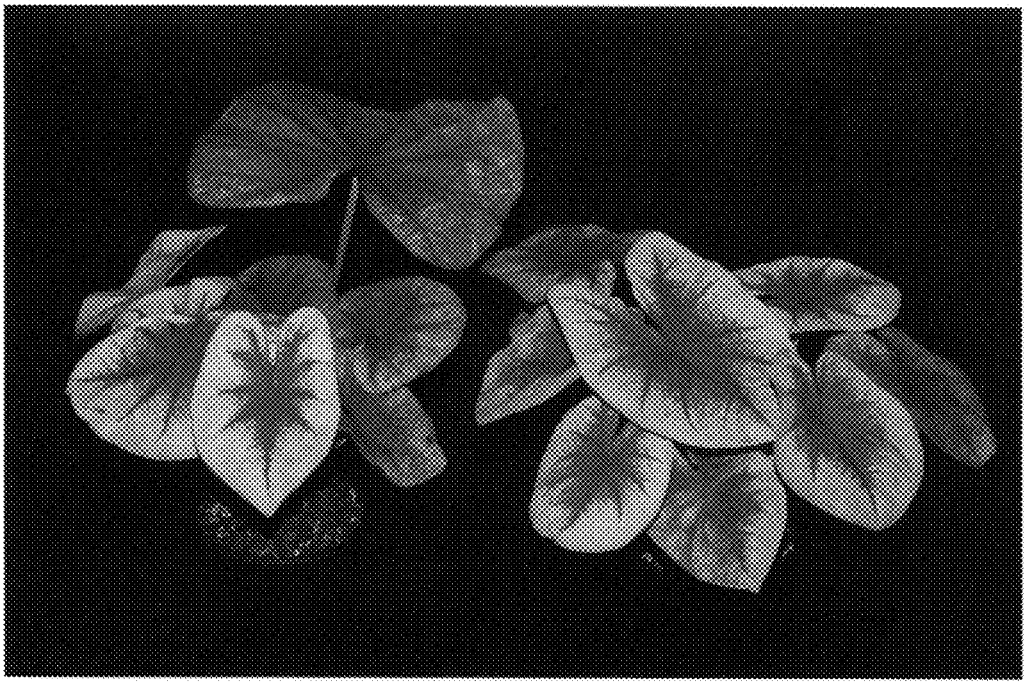
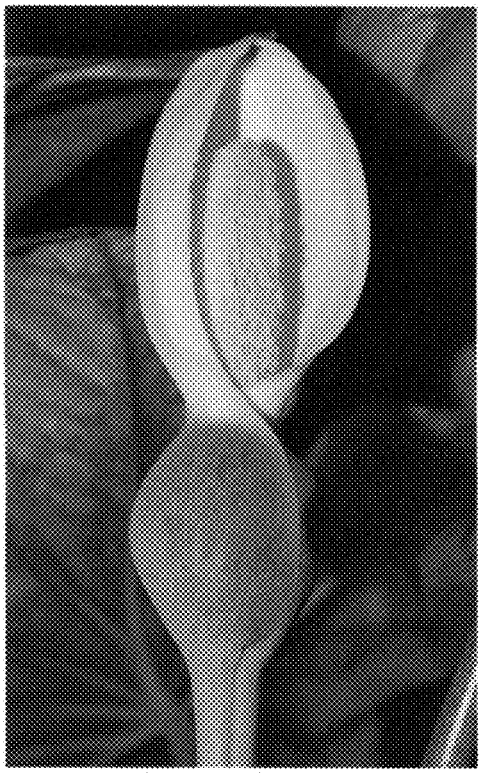

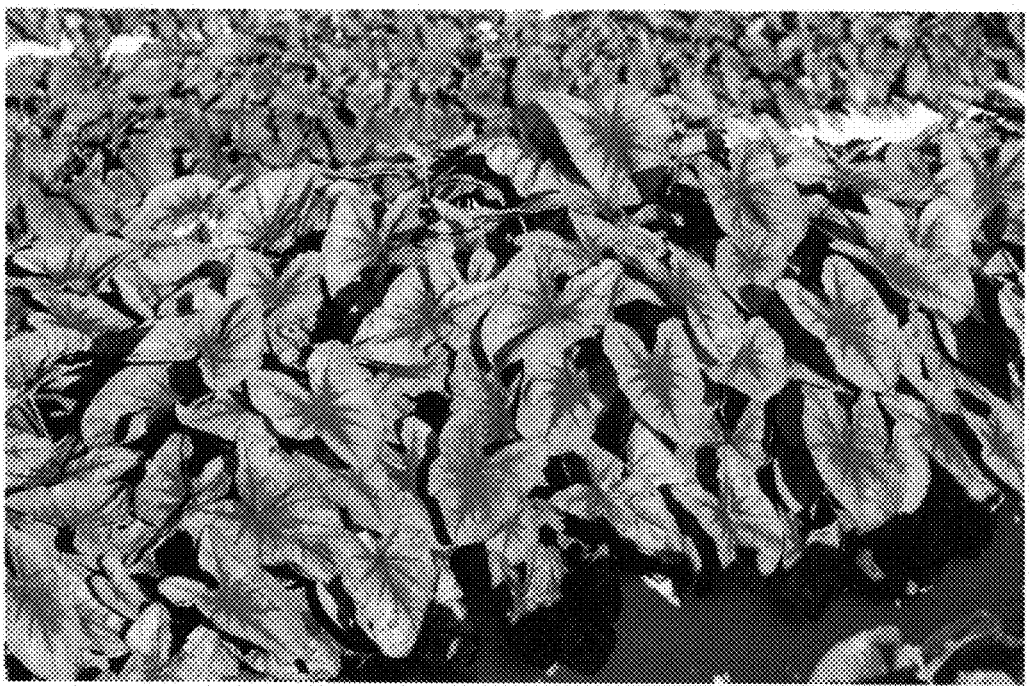
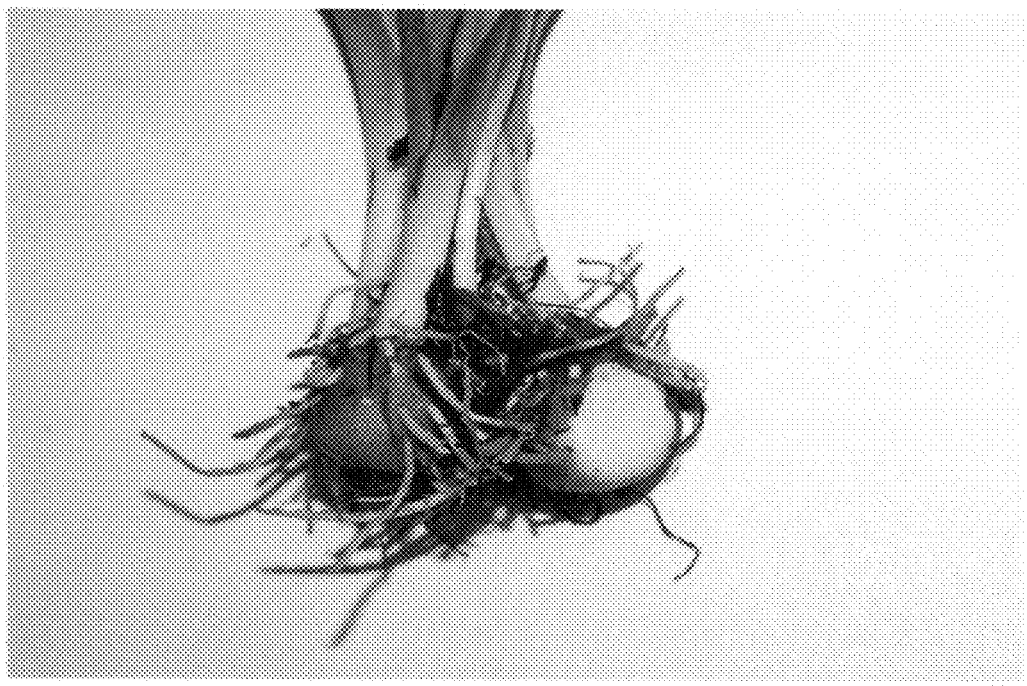

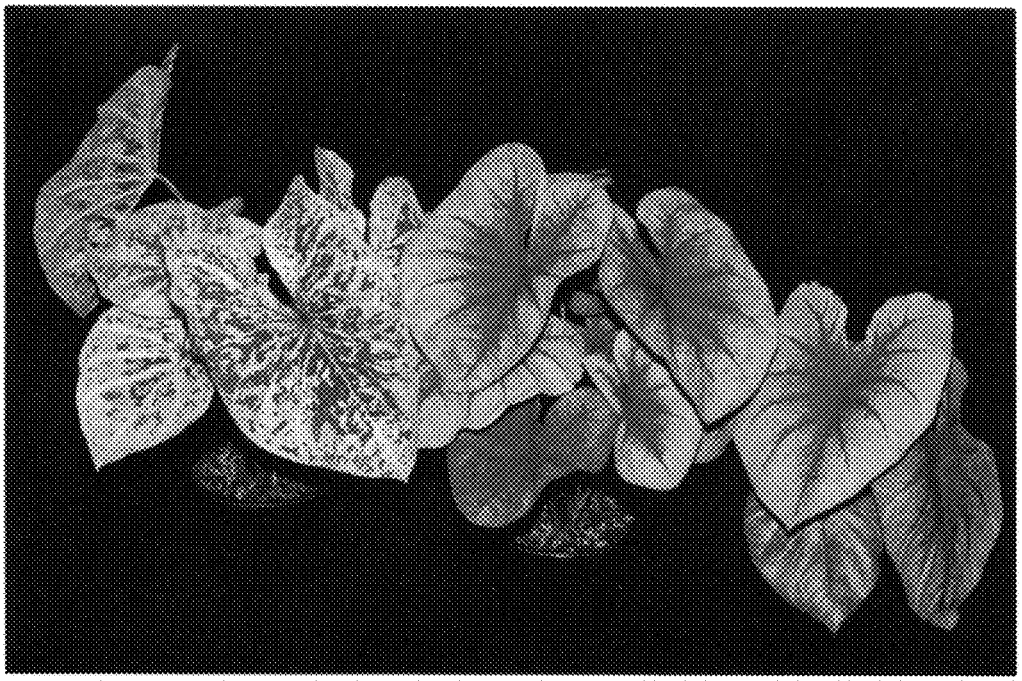
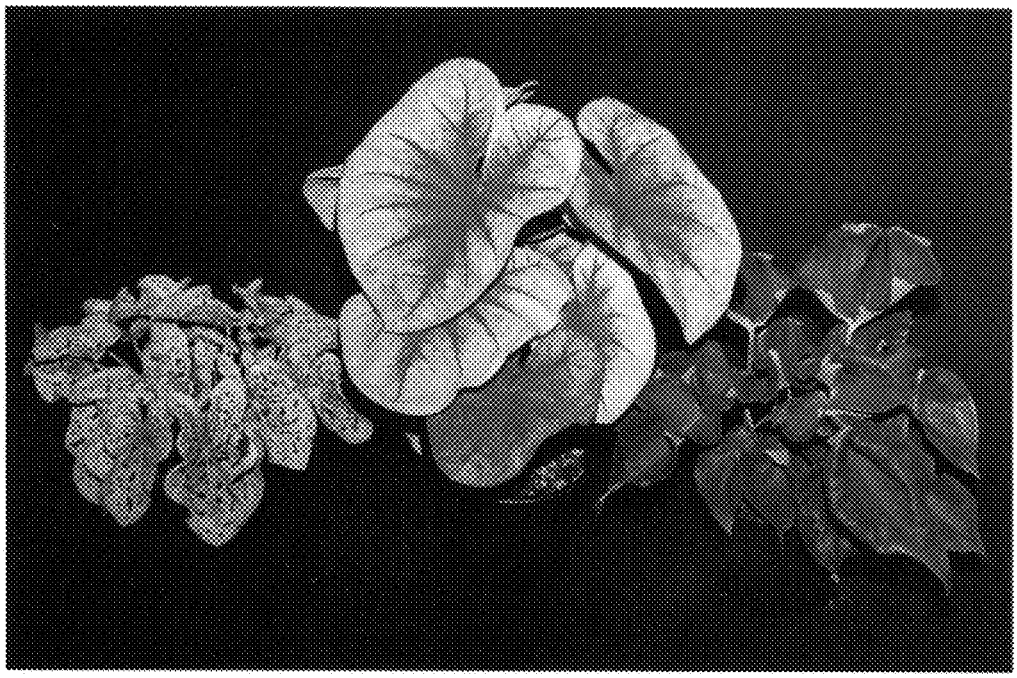

* * * * *